United States Patent [19]

Collins et al.

[11] Patent Number: 4,994,269

[45] Date of Patent: Feb. 19, 1991

[54] TOPICAL USE OF ANTIBODIES FOR PREVENTION OR TREATMENT OF PSEUDOMONAS INFECTIONS

[75] Inventors: Michael S. Collins, Pinole; Nirmal S. Mehton, Richmond, both of Calif.

[73] Assignee: Miles Inc., Elkhart, Ind.

[21] Appl. No.: 325,329

[22] Filed: Mar. 17, 1989

[51] Int. Cl.$^5$ .................... A61K 39/00; A61K 39/104
[52] U.S. Cl. .................................. 424/85.8; 435/253.3
[58] Field of Search ...................... 424/85.8; 435/253.3

[56] References Cited

U.S. PATENT DOCUMENTS 4,800,078  1/1989  Prince et al. ...................... 424/85.8

FOREIGN PATENT DOCUMENTS 2185266  7/1987  United Kingdom ............... 424/85.8

OTHER PUBLICATIONS

Bessen, J. Exp. Med., vol. 167, pp. 1945-1950, Jun. 1988.
Akerfeldt et al., Biochemical Pharmacology, vol. 22, pp. 2911-2917, 1973.

*Primary Examiner*—Howard E. Schain
*Assistant Examiner*—Choon P. Koh
*Attorney, Agent, or Firm*—James A. Giblin

[57] ABSTRACT

Method of preventing or treating a *Pseudomonas aeruginosa* infection. Method comprises topical application of antibodies to *P. aeruginos* under conditions and in an amount sufficient to prevent or treat the infection in a mammal. In one embodiment, the antibodies are administrered in form of an aerosol. A preferred dosage for polyclonal antibody preparations (i.e. ISG or high titer *P. aeruginosa* ISG) ranges from 2 mg/kg to 100 mg/kg body weight of the mammal. A preferred monoclonal antibody dosage ranges from 0.02 to 1.0 mg/kg of body weight.

13 Claims, No Drawings

TOPICAL USE OF ANTIBODIES FOR PREVENTION OR TREATMENT OF PSEUDOMONAS INFECTIONS

FIELD

This disclosure is concerned generally with the prevention or treatment of infections and specifically with the topical application of antibodies to prevent or treat infections.

PRIOR ART

Various antibody preparations have long been used to prevent or treat infections, and the preparations have been administered intramuscularly (IM) and intravenously (IV). In addition, there have been reports of topical administration of immunoglobulins to treat infections. See, for example, the topical use of immunoglobulins against viruses, Akerfeldt et al., Biochemical Pharmacology, Vol. 22, pp 2911-2917, Pergamon Press, 1973. See also the intranasal use against group A streptococci, Bessen et al., J. Exp. Med., Vol. 167, pp 1945-1950, June, 1988; the use of anti-RSV, Hemming et al. Antimicrobial Agents and Chemotherapy, pp 1269-1276, Aug. 1988; and use of antibodies against Mycoplasma pulmonis, Taylor et al., Immunology, 43, pp 519 et seq., 1981. See, also, recently issued U.S. Pat. No. 4,800,078 to G. Prince et al. (aerosol application of anti-RSV antibodies). To date, however, we are unaware of the topical application of antibody preparations to prevent or treat infections of Pseudomonas aeruginosa.

Nosocomial pneumonia is a common infection in the debilitated intensive care unit (ICU) patients. P. aeruginosa infection is a frequent cause of nosocomial pneumonia, and mortality associated with P. aeruginosa infection is approximately 70%. This death rate is about twice as high as that seen with other common ICU respiratory pathogens such as Staphylococcus, Klebsiella and Serratia.

Since the publication of the article by Köhler and Milstein, "Continuous Cultures of Fused Cells Secreting Antibody of Predefined Specificity," Nature 256:495-497 (1975), the production of monoclonal antibodies has become known and attention has been given to tailor-making high titer antibody preparations directed to a very specific antigen or a few antigens of a specific pathogen. This is being done with the hope that a highly effective prophylactic or therapeutic product will be possible for use against a very specific infection.

To avoid confusion regarding terminology, antibodies made from single cells such as the hybridomas of Köhler et al. or the later transformed cells of others (e.g. U.S. Pat. No. 4,446,465 to M. Lostrom) are all referred to as monoclonal antibodies, even if several different such antibodies are combined in a so-called cocktail (e.g. as in U.S.S.N. 734,624 filed May 15, 1985, now U.S. Pat. No. 4,834,975 filed in the name of A. Siadak et al.) describing a collection of monoclonal antibodies that bind to different antigenic determinants of P. aeruginosa. Plasma derived (Pd) antibodies are referred to as polyclonal, to describe both their wide variety and their plasma source. This also distinguishes them from monoclonal antibodies (MAbs).

By their very nature, each monoclonal antibody is directed against and binds with a single epitope on a micro-organism or other antigen. Depending upon the nature and site of the epitope, the antibody may be defined as protective or not protective.

We have found that topical application of antibodies such as intravenous IgM or IgG (IGIV) or high titered Pseudomonas intravenous IgG (Ps. IGIV) to the respiratory tract is highly effective in reducing mortality associated with such infections (e.g. P. aeruoinosa pneumonia). Our invention is especially useful when the Pseudomonas antibodies are of the IgM type which, because of their size, are difficult to deliver to the lungs via conventional systemic routes. Details of our findings are described below.

SUMMARY OF INVENTION

Our method of preventing or treating an infection in a mammal caused by P. aeruginosa comprises the step of topically applying to the site of infection in the mammal a preparation comprising antibodies that can bind to an antigen of the organism, the amount of antibodies being sufficient to prevent or treat the infection. In one preferred embodiment, an antibody preparation having a relatively high titer of antibodies to P. aeruoinosa of at least five times the normal or average titer (at least about 1 1600) is applied intranasally to treat a P. aeruginosa pneumonia. Such preparation is described by Collins and Roby, U.S. Pat. No. 4,801,450, for example, and incorporated herein by reference thereto. In another embodiment, the antibodies are administered in the form of an aerosol to the mammal's lungs. A preferred dosage for polyclonal antibody preparations ranges from about 2 mg/kg to about 100 mg/kg of body weight of the mammal, and the antibodies are part of an immune serum globulin (ISG) having an ISG content ranging from about 0.5 to about 17% on a wt/wt basis in water. A preferred dosage for monoclonal antibody preparations ranges from about 0.02 mg/kg to about 1.0 mg/kg of body weight. The antibody preparations of this disclosure may be available in a liquid form or a freeze dried form which can be reconstituted with an appropriate diluent. As used herein, the term topical, or its equivalent, means the application of antibodies to lung and airway mucosa by application via the respiratory tract (e.g. inhalation via a nebulizer or injection via a tracheal tube or bronchoscope, etc.).

As used herein, the term protective or its equivalent means capable of reducing cumulative mortality in infected animals and/or reducing bacterial inoculum within the lungs.

The term pathogen or its equivalent means a bacterium capable of causing infection in a suitable host.

Antibody preparation or its equivalent means a composition comprising antibodies from any source (e.g. plasma or monoclonal antibodies) and capable of protective binding with antigens of P. aeruoinosa bacteria.

SPECIFIC EMBODIMENTS

Our invention is illustrated with the following examples showing the intranasal application of a high titer Ps. ISG (Ps. IGIV), a conventional IGIV, a serum IgM preparation and human IgM monoclonal antibodies.

Examples

A 50 μl volume of 5% IGIV (Gamimune ®-N) or Ps. IGIV (Ps. titer at least about 1:1600) was applied to the nares of anesthetized mice. Because mice are obligate nasal breathers, the majority of the IGIV solution was aspirated into the lungs. Twenty minutes later 50 μl of Pseudomonas aeruginosa inoculum was applied to the nares; this was also aspirated into the lungs. Data in the following Tables indicate this treatment and similar treatment using monoclonal antibodies were highly effective in promoting survival in infected mice.

TABLE NO. 1

Topical polyclonal immunoglobulin promotes survival in experimental *Pseudomonas pneumonia*

| Challenge Strain | No. of Mice Dead/Total (7 Days) Treatment (mg IgG/mouse) | | | | |
|---|---|---|---|---|---|
| | Control | Ps. IGIV | | IGIV | |
| | 0 mg | 2.5 mg | 0.83 mg | 2.5 mg | 0.83 mg |
| IT 1-SK 20752 | 18/20 | 2/20 | 5/20 | 9/20 | 12/20 |
| IT 6-Davis A-5 | 17/20 | 0/20 | 0/20 | 2/20 | 3/20 |
| Total (% dead) | (88) | (5) | (13) | (28) | (38) |

Comment:
Both IGIV preparations provided significant protection. Because of its greater antibody content, Ps. IGIV would be the preferred treatment.
Data in Table No. 2 indicates Ps. IGIV and monoclonal antibody against lipopolysaccharide antigen of *P. aeruginosa* provides protection by promoting lung clearance of *P. aeruginosa*.

TABLE NO. 2

Topical Ps. IGIV and Ps. Monoclonal (MAbs) Promote Lung Clearance of *P. Aeruginosa* ATCC 27314 Inoculum

| Treatment (50 ul intranasal) | Log 10 *P. aeruginosa* in wet lung at time | | |
|---|---|---|---|
| | +1 Hr. | +4 Hrs. | +16 Hrs. |
| Ps. IVIG | | | |
| HSA in 10% Maltose | 6.53 ± 0.36* | 6.57 ± 0.62 | 10.01 ± 0.52 |
| Ps. IGIV 100 mg/kg | 6.53 ± 0.35 | 5.69 ± 0.36 | 3.95 ± 0.38 |
| Monoclonal | | | |
| 0.25% HSA in acetate buffer | 6.37 ± 0.71 | 7.00 ± 0.76 | 10.32 ± 0.65 |
| IgM MAb, ICI 2.2 mg/kg | 6.49 ± 0.75 | 6.45 ± 0.75 | 5.70 ± 0.98 |

*Geometric mean ± S.D. N = 3 mice per group
Comment:
By 16 hrs. there was a >100 − fold reduction of *P. aeruginosa* in lungs of Ps. IGIV − treated mice compared with 1 hour levels. Similarly, by 16 hrs., there was a six-fold reduction of *P. aeruginosa* in the lungs of ICI MAb-treated mice compared with one hour clearance. Also at 16 hours, there was approximately 1 million fold fewer cells in lungs of Ps. IGIV − treated mice than in lungs of control mice and approximately 42 thousand-fold fewer cells in lungs of monoclonal antibody-treated mice than in lungs of control mice.

TABLE 3A

Prophylaxis of *P. aeruginosa* immunotype 3, strain ATCC 27314, pneumonia: Topical vs. parenteral administration of Pseudomonas IGIV

| Intraperitoneal Route* | | Intranasal Route* | |
|---|---|---|---|
| Mg IgG/kg | No. mice dead/total | Mg IgG/kg | No. mice dead/total |
| 0 | 19/20 | 0 | 19/20 |
| 18 | 9/10 | 4 | 7/10 |
| 56 | 10/10 | 11 | 6/10 |
| 167 | 10/10 | 33 | 4/10 |
| 500 | 4/10 | 100 | 0/10 |
| Mean protective dose = 463 mg IgG/kg | | Mean protective dose = 32 mg/kg | |

*Ps-IGIV given by intraperitoneal route 3 hours pre infection or by intranasal route 20 min. pre infection with *P. aeruginosa*.
**P < .05 IgG treatment vs. control. P by chi square test.

TABLE 3B

Prophylaxis of *P. aeruginosa* immunotype 4, strain ATCC 27315, pneumonia: Topical vs. parenteral administration of Pseudomonas IGIV

| Intraperitoneal Route | | Intranasal Route | |
|---|---|---|---|
| Mg IgG/kg | No. mice dead/total | Mg IgG/kg | No. mice dead/total |
| 0 | 20/20 | 0 | 20/20 |
| 18 | 8/10 | 4 | 2/9** |
| 56 | 5/10** | 11 | 2/10** |
| 167 | 2/10** | 33 | 1/10** |
| 500 | 2/10** | 100 | 1/10** |
| Mean protective dose = 179 mg/kg | | Mean protective dose = <4 mg/kg | |

TABLE 3C

Prophylaxis of *P. aeruginosa* immunotype 6, strain A5, pneumonia: Topical vs. parenteral administration of Pseudomonas IGIV

| Intraperitoneal Route | | Intranasal Route | |
|---|---|---|---|
| Mg IgG/kg | No. mice dead/total | Mg IgG/kg | No. mice dead/total |
| 0 | 20/20 | 0 | 20/20 |
| 18 | 8/10 | 4 | 1/10** |
| 56 | 6/10** | 11 | 0/10** |
| 167 | 2/10** | 33 | 0/10** |
| 500 | 2/10** | 100 | 0/10** |
| Mean protective dose = 192 mg/kg | | Mean protective dose = <4 mg/kg | |

TABLE 4A

Prophylaxis of *P. aeruginosa* immunotype 3, strain ATCC 27314, pneumonia: Topical vs. parenteral administration of anti-immunotype 3 LPS human IgM monoclonal antibody, ICI

| Intraperitoneal Route* | | Intranasal Route* | |
|---|---|---|---|
| Mg IgG/kg | No. mice dead/total | Mg IgG/kg | No. mice dead/total |
| 0.00 | 18/20 | 0 | 18/20 |
| 0.07 | 8/10 | 0.04 | 3/10** |
| 0.22 | 10/10** | 0.12 | 3/10** |
| 0.67 | 8/10 | 0.35 | 1/10** |
| 2.00 | 3/10** | 1.04 | 0/10** |
| Mean protective dose = 1.45 mg IgM/kg | | Mean protective dose = <0.04 mg IgM/kg | |

*ICI given by intraperitoneal route 3 hours pre infection or by the intranasal route 20 min. pre infection with *P. aeruginosa*
**P < .05 ICI treatment vs. control. P by chi square test.

TABLE 4B

Prophylaxis of *P. aeruginosa* immunotype 6, strain A5, pneumonia: Topical vs. parenteral administration of anti-immunotype 6 LPS human IgM monoclonal antibody 5G2

| Intraperitoneal Route | | Intranasal Route | |
|---|---|---|---|
| Mg IgG/kg | No. mice dead/total | Mg IgG/kg | No. mice dead/total |
| 0.0 | 18/20 | 0 | 18/20 |
| 0.07 | 9/10 | 0.04 | 1/10** |
| 0.22 | 9/10 | 0.12 | 0/10** |
| 0.67 | 4/10** | 0.35 | 1/10** |
| 2.00 | 1/10** | 1.04 | 0/10** |
| Mean protective dose = 0.92 mg IgM/kg | | Mean protective dose = <0.04 mg IgM/kg | |

TABLE 5

Summary: Mean protective dose of parenteral vs. intranasal administered immunoglobulin

| Immuno-globulin | P. aeruginosa Challenge Strain | Mean protective dose by route (mg/kg) | | Fold Difference Parenteral Intra-nasal |
|---|---|---|---|---|
| | | Intra-peritoneal | Intra-nasal | |
| Pseudomonas IGIV | Immunotype 3 ATCC 27314 | 463 | 32 | 14.5 X |
| Pseudomonas IGIV | Immunotype 4 ATCC 27315 | 179 | <4 | >44.8 X |
| Pseudomonas IAIV | Immunotype 6 A5 | 192 | <4 | >48.0 X |
| Monoclonal IgM, ICI | Immunotype 3 ATCC 27314 | 1.45 | <0.04 | >36.3 X |
| Monoclonal IgM, 5G2 | Immunotype 6 A5 | 0.92 | <0.04 | >23.0 X |

FURTHER EXAMPLES

In yet another experiment, we found that a plasma derived IgM preparation was similarly protective, as shown in Table 6, below. The plasma IgM was prepared in accordance with commonly assigned patent application application Ser. No. 203,377, filed in names of Collins et al. and entitled, Therapeutic IgM Concentrates. The actual plasma derived IgM product consisted of about 0.8% wt/vol protein solution, containing about 95% IgM with trace amounts of IgA and IgG antibodies. The solution was at pH 4.8 and included 0.25 M glycine as a stabilizer.

TABLE 6

Topical IgM Prophylaxis of P. aeruginosa immunotype 3, strain ATCC 27314, pneumonia.

| P. aeruginosa ATTC 27314 cfu IN. | No. Mice Dead/Total Treatment* | |
|---|---|---|
| | Control 0 mg | Plasma IgM 13.4 mg IgM/kg |
| 5.8 × 10$^6$ | 10/10 | 1/10 |

*Pd. IgM or saline in 50 μl given by intranasal route 20 minutes before challenge.

Our data indicate that topical immunoglobulin is highly effective in preventing mortality associated with Pseudomonas pneumonia. For prevention of Pseudomonas pneumonia in high-risk hospital patients, immunoglobulin could easily be administered by aerosol (via nebulizer). Similarly, topical immunoglobulin may be useful in preventing recurrent pneumonia in patients with cystic fibrosis whose lungs are chronically colonized with P. aeruginosa. Furthermore, serum immunoglobulin or monoclonal antibodies, could be specifically formulated with suitable pharmaceutically acceptable excipients for aerosol administration.

It is thought that a topical or aerosol administration of antibodies specific to P. aeruginosa would be similarly effective using a wide variety of excipients or vehicles to assure even and non-detrimental distribution of the antibody preparation. These could be readily formulated by those skilled in the art.

As noted above, our method is especially advantageous in administering antibodies of the IgM type directly to the lung. Also, our method permits ease of use, and less antibody is needed since it is not delivered systemically. In addition, our method avoids trauma, prevents sepsis or injuries associated with venipuncture, is faster and can be used in cases where an IV administration is very difficult (in cases of collapsed veins or for obese people whose veins are difficult to find).

Given the above disclosure, it is thought that variations will occur to those skilled in the art. Accordingly, it is intended that the invention disclosed here should be limited only by the following claims.

We claim:

1. A method of preventing infection of Pseudomonas aeruginosa bacteria in a mammal, the method of comprising the topical application of antibodies capable of binding to an antigen of the Pseudomonas aeruginosa bacteria prior to exposure to the bacteria by the mammal, the antibodies being of the IgM or IgG type and the amount of antibodies being sufficient to provide prophylactic protection against the bacteria.

2. The method of claim 1 wherein the antibodies are selected from monoclonal antibodies, an immune serum globulin and a high titer Pseudomonas aeruginosa immune serum globulin.

3. The method of claim 2 wherein the Pseudomonas aeruginosa immune serum globulin has an antibody titer of at least 1:1600 against Pseudomonas aeruginosa.

4. The method of claim 2 wherein the antibodies are administered intranasally to the mammal.

5. The method of claim 2 wherein the antibodies are administered in the form of an aerosol to the lungs of the mammal.

6. The method of claim 2 wherein the antibodies are plasma derived and administered at a dosage ranging from about 2 mg/kg to about 100 mg/kg of body weight of the mammal.

7. The method of claim 2 wherein the antibodies are monoclonal antibodies and administered at a dosage ranging from about 0.02 to about 1.0 mg/kg of body weight of the mammal.

8. The method of claim 2 wherein the immune serum globulins comprises an aqueous solution of antibodies having an antibody content ranging from about 0.5 to about 17% by weight of the solution.

9. The method of claim 1 wherein the antibodies are of the IgM type.

10. The method of claim 1 wherein the antibodies are of the IgG type.

11. The method of claim 1 wherein the antibodies of a mixture of antibodies of the IgM and IgG types.

12. The method of claim 2 wherein the antibodies are administered via intratracheal administration means.

13. The method of claim 8 wherein the antibody solution is prepared by reconstituting a freeze dried antibody preparation with a diluent.

* * * * *

UNITED STATES PATENT AND TRADEMARK OFFICE
CERTIFICATE OF CORRECTION

PATENT NO. : 4,994,269

DATED : February 19, 1991

INVENTOR(S) : Michael S. Collins et al

It is certified that error appears in the above-identified patent and that said Letters Patent is hereby corrected as shown below:

ON THE TITLE PAGE,
IN THE ABSTRACT:

At line 3, "aeruginos" should be --aeruginosa--.

At Col. 2, line 24, "1 1600" should be --1:1600--.
At Col. 3, line 24, "Aeruginosa" should be --aeruginosa--.

Signed and Sealed this

Fourteenth Day of July, 1992

*Attest:*

DOUGLAS B. COMER

*Attesting Officer*  Acting Commissioner of Patents and Trademarks